United States Patent [19]

Morinaka et al.

[11] Patent Number: 4,668,677
[45] Date of Patent: May 26, 1987

[54] 4-PHENYLPHTHALAZINE DERIVATIVES, THEIR PREPARATION AND THEIR USE AS PHARMACEUTICALS

[75] Inventors: Yasuhiro Morinaka; Katsuhiko Iseki; Toshiji Kanayama; Toshiaki Watanabe; Hiroyoshi Nishi, all of Ami, Japan

[73] Assignee: Mitsubishi Chemical Industries Limited, Tokyo, Japan

[21] Appl. No.: 722,304

[22] Filed: Apr. 11, 1985

[30] Foreign Application Priority Data

Apr. 16, 1984 [JP] Japan .................................. 59-75161

[51] Int. Cl.$^4$ .................. C07D 237/34; C07D 237/30; A61K 31/50
[52] U.S. Cl. ...................................... 514/248; 544/237
[58] Field of Search ......................... 544/237; 514/248

[56] References Cited

U.S. PATENT DOCUMENTS 3,274,185  9/1966  Sigal, Jr. ............................. 544/237

FOREIGN PATENT DOCUMENTS 1303061  1/1983  United Kingdom ................ 544/237

*Primary Examiner*—Mark L. Berch
*Attorney, Agent, or Firm*—Frishauf, Holtz, Goodman & Woodward

[57] ABSTRACT

Certain new 1-alkylamino-4-phenylphthalazine derivatives, 1-neopentylamino-4-phenylphthalazine and 1-(1-ethylpropylamino)-4-phenylphthalazine, having prominent activity to ameliorate circulatory disorders and prepared from the corresponding phthalazinones.

7 Claims, No Drawings

4-PHENYLPHTHALAZINE DERIVATIVES, THEIR PREPARATION AND THEIR USE AS PHARMACEUTICALS

BACKGROUND OF THE INVENTION

This invention relates to a certain group of new 4-phenylphthalazine derivatives, a process for preparing the same and their use as pharmaceuticals.

The compounds of this invention are a novel class of the 1-alkylamino-4-phenylphthalazine derivatives and pharmaceutically acceptable salts thereof and show valuable therapeutic activities, especially activity to improve or ameliorate circulatory disorders or dysfunctions.

In the prior art, there have been proposed in British Pat. No. 1,303,061 a series of 1-alkylamino-4-phenylphthalazine derivatives having the formula

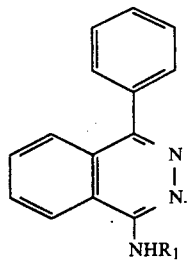

In said British Patent, there are illustratively disclosed as $R_1$ a methyl, ethyl, n-propyl, isopropyl, isobutyl or hexyl group; however, only the version "amyl group" is disclosed therein for an alkyl group having 5 carbon atoms and no concrete disclosure is seen with regard to its isomerism. Moreover, said British Patent discloses that the derivatives have an anti-inflammatory activity, but it does not disclose or teach any other pharmacological activities of the derivatives. Further, it is disclosed in said British Patent that the compounds having the above formula wherein the substituent $R_1$ is an alkyl group having 1 to 4 carbon atoms are preferable of those compounds (said British Patent Specification, page 2, left column, line 34), but it is to be noted that an alkyl group having 5 carbon atoms, namely an amyl group is clearly excluded from the preferred perview of groups for $R_1$. On the other hand, there are disclosed in J. Med. Chem., 12, 555 (1969) those compounds of the above formula wherein $R_1$ is a cyclopentyl group, together with other derivatives; however, an anti-inflammatory activity solely is disclosed therein as pharmacological activities.

For drugs or medicaments, which may be applied in prophylatic and therapeutic treatments of ischemic cardiac diseases such as myocardial infarction or angina pectoris, circulatory disorders or dysfunctions such as cerebral and peripheral circulatory disturbance in cerebral thrombosis or cerebral embolism, there should be required the activity to increase blood flow volume at the disturbed sites, the anti-thrombic activity as well as the basic activity therefor, i.e., the vasodilation activity and the activity to inhibit blood platelet aggregation. Thus, there has been desired such a compound that has all activities as noted above together. Also, as prolonged administration of drugs in necessary for prophylatic and therapeutic treatments of the aforesaid diseases, it is significant that such a type of drugs should have a lower toxicity.

As reported in "Drugs, 18, 439 (1979), many anti-inflammatory agents such as aspirin or indomethacin are known to show the activity to inhibit blood platelet aggregation, but the mode of action thereof is attributed to the action to inhibit cyclooxygenase and consequently inhibit biosynthesis of prostaglandins as seen for anti-inflammatory agents [vide, Pharmacol. Rev., 26, 33 (1974)]. Consequently, they are not desirable as a circulatory disorder improving agent, because not only thromboxane $A_2$, a substance inducing blood platelet aggregation and vasoconstriction, but also biosynthesis of prostaglandin $I_2$ (hereinafter referred to as "$PGI_2$"), which exhibits an action opposit to that of thromboxane $A_2$ in blood platelets and blood vessels, could be simultaneously inhibited.

And yet, aspirin or indomethacin does not show at all the activity to increase blood flow ["Prostaglandins", 25, 549 (1983)] and it is further reported that indomethacin did decrease a topical blood flow in brain on the contrary [Am. J. Physiol., 243, H416, (1982)].

The present inventors previously found that some 1-anilino-4-phenylphthalazine derivatives show a potent activity to inhibit blood platelet aggregation in vitro, as seen in Japanese Patent Laid-open Application Nos. 53659/1981, 53660/1981 and 48972/1982. However, other circulatory dysfunction improving actions than the action to inhibit blood platelet aggregation are not disclosed at all in these Japanese Application.

SUMMARY OF THE INVENTION

Then, the present inventors have made earnest studies to obtain the compound having all circulatory disorder ameliorating actions as discussed above and a lower toxicity. As a result, they have successfully synthesized novel compounds, namely, 1-neopentylamino-4-phenylphthalazine and 1-(1-ethylpropylamino)-4-phenylphthalazine and we have also found that they have the activity to increase blood flow, the antithrombic activity and the activity to inhibit blood platelet aggregation and they show a much more potent effect and a lower toxicity, as compared with other 1-alkylamino-4-phenylphthalazine analogues. This invention has been completed upon the above-mentioned findings.

It is accordingly a primary object of this invention to provide novel 1-alkylamino-4-phenylphthalazine compounds having valuable activities to improve circulatory disorders.

DESCRIPTION OF THE PREFERRED EMBODIMENTS

According to this invention, there is provided a 1-alkylamino-4-phenylphthalazine compound having the formula (I)

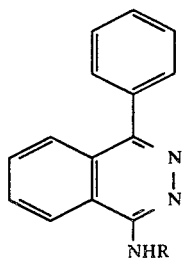

(wherein R represents a neopentyl group or a 1-ethylpropyl group) and a pharmaceutically acceptable salt thereof, a process of the preparation thereof and a circulatory disorder improving agent which comprises the same as an active ingredient.

As pharmaceutically acceptable salts of the present compounds having the formula (I), there may be mentioned those salts with mineral acids such as hydrochloric acid, hydrobromic acid, sulfuric acid, phosphoric acid and the like or with organic acids such as methanesulfonic acid, p-toluenesulfonic acid, benzenesulfonic acid, acetic acid, glycolic acid, glucronic acid, maleic acid, fumaric acid, citric acid, ascorbic acid, oxalic acid, salicylic acid, nicotinic acid, tartaric acid and the like.

The compounds of the present invention may be prepared according to any optional purposive process. Preferable processes will be illustratively disclosed hereinbelow.

Method A

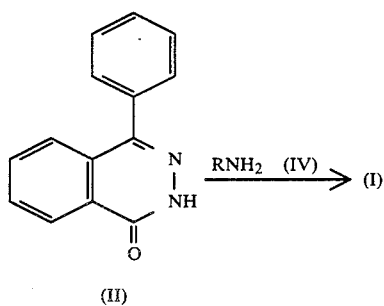

(wherein R is as defined above).

In this method, the compound of the present invention is prepared by reacting the starting 4-phenyl-1(2H)-phthalazinone with neopentylamine or 1-ethylpropylamine in the presence or absence of a solvent and in the presence of a phosphorus compound or a sulfur compound.

The starting material, 4-phenyl-1(2H)-phthalazinone, can be synthesized according to the process disclosed in "Yakugaku Zasshi" (the Journal of the Pharmaceutical Society of Japan, in Japanese), 86, 576 (1966).

Reaction temperature is usually −20° C. to 250° C., preferably −10° C. to 200° C. and reaction period of time is usually 5 minutes to 24 hours, preferably 10 minutes to 10 hours.

As phosphorus or sulfur compounds which may be employed in this reaction, there may be mentioned, for example, phosphorus oxychloride, phosphorus trichloride, phosphorus pentachloride, phosphorus tribromide, phosphorus triiodide, diphenyl chlorophosphate, diethyl chlorophosphate, diethyl chlorophosphite, polyphosphoric acid, thionyl chloride and the like. The compound may be usually at a molar ratio of 0.5 to 5, preferably 0.5 to 3, per mole of the starting material (II).

Where a solvent is employed, there may be used, for example, ethers such as ethyl ether, tetrahydrofuran, dioxane; halogenated hydrocarbons such as chloroform, methylene chloride; aromatic hydrocarbons such as benzene, toluene, xylene, bromobenzene; amides such as dimethylformamide, acetamide; sulfoxides such as dimethyl sulfoxide and the solvent may be usually employed at a weight ratio of 1 to 100 per unit weight of the starting material (II).

In this method, it is preferable to employ a base catalyst; in this instance, there may be applied as the catalyst organic bases such as triethylamine, pyridine or inorganic bases such as $NaHCO_3$, $Na_2CO_3$, $K_2CO_3$, NaOH, KOH, NaH, $NaNH_2$, which may be usually employed at a molar ratio of 0.5 to 5, preferably 1 to 3, per mole of the starting material (II).

An amount of neopentylamine or 1-ethylpropylamine to be used is usually of a molar ratio of 0.5 to 30, preferably 1 to 20, per mole of the starting material (II).

After completion of the reaction, the reaction product may be recovered and purified according to any conventional procedures; for example, the reaction mixture is poured into a large excess of water or extracted with a suitable solvent, e.g. chloroform and neutralized with an alkali aqueous solution followed by recrystallized or chromatography.

Method B

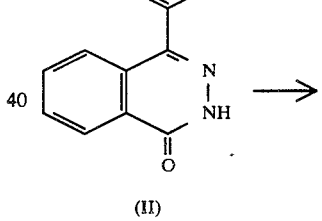

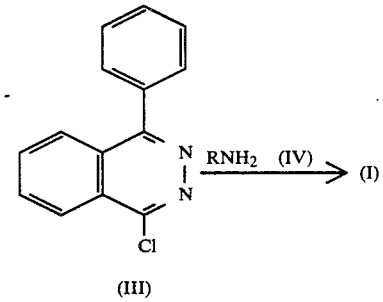

(wherein R is as defined above).

In this method, the said starting material (II) is first converted to 1-chloro-4-phenylphthalazine (III) according to the process described in "Yakugaku Zasshi", 86, 576 (1966) and then the latter product is reacted with neopentylamine or 1-etheylpropylamine in the presence or absence of a solvent and, preferably, in the presence of a catalyst.

Solvents, catalysts, and other reaction conditions (e.g., reaction temperature, reaction period) may be the same as stated above with regard to Method A. The desired product may be recovered and purified in the same manner as in Method A.

For practical application of the compounds of the present invention as a circulatory disorder improving agent, they may be administered medically by the normal oral, parenteral and enteral routes. For oral administration, the active compound may be preferably administered at a single dose for adults of 1 mg to 100 mg once to three times daily. For intravenous administration, the active compound may be preferably given at a single dose for adults of 0.01 mg to 10 mg two to five times daily. For rectal administration, the active compound may be preferably given at a single dose for adults of 1 mg to 100 mg once to three times daily. However, the dose will more preferably vary depending upon the severity of condition and the age and body weight of the patient.

It is usual that we may use a pharmaceutical composition which comprises at least one of the compound of the above formula (I) and a pharmaceutically acceptable salt thereof, together with a conventional pharmaceutical carrier or excipient and other suitable additives.

Pharmaceutical carrier may be either solid or liquid. As examples of solid carrier, there may be mentioned lactose, kaolin, sucrose, crystalline cellulose, corn starch, talc, agar, pectin, acacia, stearic acid, magnesium stearate, lecithin or sodium chloride. As examples of liquid carrier, there may be mentioned syrup, glycerol, peanut oil, polyvinyl pyrrolidone, olive oil, ethanol, benzyl alcohol, propylene glycol or water.

Pharmaceutical compositions may be of various types of formulations. If a solid carrier is used, one may employ the form of tablets, powders, granules, hard gelatin capsules, suppositories or troches and an amount of the solid carrier to be applied may vary over a wide range, preferably about 1 mg to about 1 g. If a liquid carrier is used, one may employ the form of syrups, emulsions, soft gelatin capsules, sterile injectable solutions or aqueous or non-aqueous suspensions.

Alternatively, the active compound may be also applied in the form of an inclusion compound thereof with cyclodextrin or in liposome.

The compounds of the present invention, as briefed hereinabove, have the activity to increase blood stream, to inhibit the aggregation of blood platelets and to inhibit thrombosis and show a high superiority in effects and toxicity, as compared with other analogous 1-alkylamino-4-phenylphthalazine compounds, so that they have excellent properties as a circulatory disorder or dysfunction—improving agent.

This invention will be more fully illustrated by way of the following non-limiting Examples.

EXAMPLE 1

Preparation of 1-neopentylamino-4-phenylphthalazine

To a suspension of 100 g of 4-phenyl-1(2H)-phthalazinone and 96.2 g of neopentylamine in 300 ml of p-xylene were added dropwise 83.7 g of phosphorus oxychloride with stirring and the resulting mixture was stirred under reflux for 4 hours. After allowing to be cooled, a saturated aqueous solution of $NaHCO_3$ was added to the reaction mixture. Then, the mixture was extracted with chloroform and the organic layer was separated, dried and then concentrated. The residue was recrystallized from ethanol to afford the title compound as a pale yellow crystal. 100.8 g (Yield, 77%) Melting point: 215.5°–216.5° C.

Infrared spectrum: 3240, 2950, 1570, 1515, 775, 695 $cm^{-1}$.

Mass spectrum: 291 (M+), 276, 261, 234, 220, 205, 77.

EXAMPLE 2

Preparation of 1-(1-ethylpropylamino)-4-phenylphthalazine

By the same procedures as in Example 1 except that 1-ethylpropylamine was employed in lieu of the neopentylamine, there was obtained the title compound.

Melting point: 209.5°–210° C.

Infrared spectrum: 3250, 2950, 1555, 1507, 1145, 775, 695 $cm^{-1}$.

Mass spectrum: 291 (M+), 276, 262, 221, 205, 165, 77.

EXAMPLE 3

(1) Activity to inhibit the aggregation of blood platelets and acute toxicity of the present compounds and other 4-phenylphthalazine derivatives Male Wistar-ST strain rats of an average body weight of 250 g were used, a group consisting of 8 animals. The test compound indicated in the following Table 1 was orally administered to rats in the form of a suspension in a 1% tragacanth aqueous solution at 4 ml/Kg (the test compound 10 mg/Kg).

One hour after the administration, blood samples were obtained from the carotid artery by means of a cannule. Blood samples were collected into plastic test tubes containing 3.8% sodium citrate (1/10 volume). Tubes were turned upside-down and then subjected to centrifugation at 200×g over 15 minutes to assign the supernatant as a platelet-rich plasma (PRP). The residue was further centrifuged at 20033 g over 15 minutes to assign the supernatant as a platelet-poor plasma (PPP). These supernatants were applied for determining the ability to aggregate blood platelets. For this determination purpose, a 2-channels blood platelet aggregometer (DP 247 E type, by Sienco Co., Ltd.) was used to make records on a 2-pens type recorder. As an aggregation inducing agent, collagen (availale from Hormon-chemie A.G.) was used at a concentration of 7 to 10 $\mu g/ml$.

Inhibitory rate to aggregate blood platelets was calculated according to the following equation:

$$\text{Inhibitory Rate} = \frac{A - B}{A} \times 100 \ (\%)$$

A: Inhibitory rate in the group to which the 1% tragacanth solution alone was given (Control)

B: Aggregation rate in the group to which the tragacanth solution of the test compound was given.

The results are shown in Table 1, together with acute toxicity ($LD_{50}$) to rats.

TABLE 1

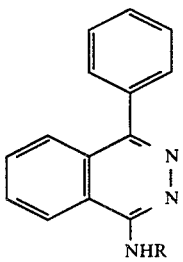

| Test compound | R | Inhibitory rate | LD$_{50}$ (mg/Kg, p.o.) |
|---|---|---|---|
| Compounds of this invention | | | |
| 1 | —CH$_2$C(CH$_3$)$_3$ | 100 | >8000 |
| 2 | —CH(CH$_2$CH$_3$)$_2$ | 70.1 | >8000 |
| Comparative compounds | | | |
| 1 | —(CH$_2$)$_2$CH$_3$ | 27.6 | 522 |
| 2 | —CH(CH$_3$)$_2$ | 7.1 | |
| 3 | —(CH$_2$)$_3$CH$_3$ | 0 | |
| 4 | —CH$_2$CH(CH$_3$)$_2$ | 0 | |
| 5 | —CH(CH$_3$)CH$_2$CH$_3$ | 0 | |
| 6 | —C(CH$_3$)$_3$ | 0 | |
| 7 | —(CH$_2$)$_4$CH$_3$ | 6.2 | 1780 |
| 8 | —CH(CH$_3$)(CH$_2$)$_2$CH$_3$ | 0 | |
| 9 | —CH$_2$CH(CH$_3$)CH$_2$CH$_3$ | 79.2 | 2181 |
| 10 | —CH(CH$_3$)CH(CH$_3$)$_2$ | 54.1 | 2528 |
| 11 | —(CH$_2$)$_2$CH(CH$_3$)$_2$ | 24.0 | |
| 12 | —C(CH$_3$)$_2$CH$_2$CH$_3$ | 0 | |
| 13 | cyclopentyl | 0 | |
| 14 | —(CH$_2$)$_5$CH$_3$ | 15.6 | |
| 15 | —CH$_2$CH(CH$_2$CH$_3$)$_2$ | 14.6 | |
| 16 | —CH(CH$_3$)CH$_2$CH(CH$_3$)$_2$ | 0 | |
| 17 | —(CH$_2$)$_2$C(CH$_3$)$_3$ | 17.3 | |
| 18 | cyclohexyl | 0 | |
| 19 | —(CH$_2$)$_6$CH$_3$ | 0 | |
| 20 | —(CH$_2$)$_7$CH$_3$ | 0 | |

(2) Activity to inhibit the blood platelet adhesion

As experimental animals, there were used male Wistar-ST strain rats of an average body weight of 250 g.

Blood samples were obained from carotid arteries by means of a cannule and immediately admixed with sodium citrate at a volume ratio of 1/10. The mixture was centrifuged at 200×g over 15 minutes to collect the supernatant (platelet-rich plasma: PRP). The PRP was then centrifuged at 2000×g over 15 minutes and the supernatant was removed to give blood platelet pellet.

To the resultant blood platelet pellet was added a 15 mM tris.HCl buffer solution with EDTA (pH 7.4) to resuspend blood platelets therein and then one applied centrifugation at 2000×g over 15 minutes and the supernatant was removed. The resultant washed blood platelets were added to a 0.3 mM tris.HCl buffer solution with CaCl$_2$ (pH 7.4) to resuspend blood platelets therein, whereby there was prepared a blood platelet suspension adjusted to five hundred thousand platelets/μl. To 2 ml of the blood platelet suspension were added 2 μl of a methanolic solution of each test compound and incubation was effected for 15 minutes. Then blood platelet adhesion was determined according to a glass bead method by using a timing blood suction apparatus for determining the blood platelet adhesion.

The number of blood platelets was counted by means of a blood platelet counter.

Inhibitory rate of blood platelet adhesion was calculated according to the following equation:

$$\text{Inhibitory rate of adhesion} = \frac{A - B}{A} \times 100\ (\%)$$

A: Blood platelet number in the blood platelet suspension passed through a control column
B: Blood platelet number in the blood platelet suspension passed through a bead-packing column The results are shown in Table 2.

TABLE 2

| Test compound | Inhibitory rate (%) | | | |
|---|---|---|---|---|
| | $3 \cdot 10^{-7}$ M | $3 \cdot 10^{-6}$ M | $3 \cdot 10^{-5}$ M | $3 \cdot 10^{-4}$ M |
| Compound 1 of this invention | 8.2 | 12.5 | 40.8 | 50.2 |
| Aspirin | 3.5 | 8.4 | 5.3 | 4.0 |
| Ticlopidine | 2.4 | 11.0 | 7.0 | 9.3 |

From the Table 2, it can be seen that the compounds of this invention inhibit a blood platelet adhesion with dose dependence and show an excellent effect, as compared with other blood platelet function inhibitors, namely aspirin and ticlopidine.

(3) Anti-thrombotic activity

Male ICR-JCL strain mice with an average body weight of about 25 g and male New Zealand White rabbits with an average body weight of about 3 Kg were used.

Where mice were used as experimental animals, a suspension of the test compound indicated in Table 3 in a 1% tragacanth aqueous solution was orally administered to animals at 20 ml/Kg. One hour after the administration, an arachidonic acid (PL-biochemical Co., Inc.) solution dissolved in a 0.1M sodium carbonate aqueous solution was intravenously given at 100 mg/Kg. Evaluation of activity was effected with the time from the administration of arachidonic acid up to the death of animals as well as mortality. The results are shown in Table 3.

Where rabbits were used as experimental animals, a suspension of the test compound in a 1% tragacanth aqueous solution was orally administered to animals at 5 ml/Kg. Two hours after the administration, an arachidonic acid solution dissolved in a 0.1M potassium carbonate solution was injected into pinna vein at 1.4 mg/Kg.

Evaluation of activity was effected with mortality at the time when arachidonic acid given. If survived at the first administration of arachidonic acid, arachidonic acid was administered after 6 hours, 24 hours, 48 hours and 72 hours from the administration of the test compound, respectively, and mortality was determined in respective cases. The results are shown in Table 4.

TABLE 3

| Test compound | Dose (mg/Kg) | Number of mice | Mortality (%) | Survival time* (second) |
|---|---|---|---|---|
| Compound 1 of this invention | 30 | 8 | 75 | 101 ± 11 |
| | 100 | 8 | 75 | 108 ± 11 |
| | 300 | 8 | 0 | |
| 2 | 10 | 7 | 86 | 127 ± 14 |
| | 30 | 7 | 86 | 127.5 ± 14 |
| | 100 | 7 | 0 | |
| | 300 | 7 | 0 | |
| Aspirin | 100 | 8 | 100 | 322 ± 103 |
| | 300 | 8 | 37.5 | 180 ± 67 |
| Ticlopidine | 300 | 8 | 100 | 81 ± 13 |
| | 1000 | 8 | 100 | 128 ± 18 |
| Non-medicated groups | | 8 | 100 | 95 ± 6 |

*Survival time of dead mice

TABLE 4

| Test compound | Dose (mg/Kg) | No. of rabbits | After administration of test compound (hrs.) | | | | |
|---|---|---|---|---|---|---|---|
| | | | 2 | 6 | 24 | 48 | 72 |
| Compound 1 of this invention | 10 | 4 | 1 | 2 | 1 | | |
| | 30 | 8 | | | 3 | 1 | 4 |
| 2 | 3 | 4 | 2 | 1 | 1 | | |
| | 10 | 4 | | 4 | | | |
| | 30 | 4 | | | | 2 | 2 |
| Ticlopidine | 30 | 4 | 4 | | | | |
| | 100 | 4 | 3 | 1 | | | |
| Non-medicated groups | | 40 | 40 | | | | |

(4) Influence on production PGI$_2$-like substance in vessel walls

Male Wistar-ST strain rats with an average weight of about 250 g were used as experimental animals. After fasted for 18 hours, 6.3 ml of blood sample were obtained from corotid artery and immediately thereafter 0.7 ml of an anticoagulant (3.8% sodium citrate) was added and the sample was centrifuged at 200×g over 15 minutes to take platelet-rich plasma (PRP). The same procedures as above were carried out, using 5 to 6 rats, whereby 5-6 ml as normal PRP were stored and employed.

Reference aggregation values were determined by pouring 1 ml each of stored PRP into plastic test tubes, incubating them at 22° C. for 10 minutes and then determining aggregation rate. As an aggregation inducing agent, one employed 10 μM ADP (available from Sigma Co., Inc.)

A suspension of the compound of this invention or aspirin in a 1% aqueous solution of tragacanth was orally given to animals. After 1 hour, 5 mg of carotid artery were cut out in a ring shape and placed into a plastic test tube together with 1 ml of stored PRP. After incubated at 22° C. for 10 minutes, aggregation rate was determined.

Also, non-medicated groups were similarly treated and aggregation rate was determined.

Determination of blood platelet aggregation rate was made by means of an aggregometer.

The results are shown in Table 5, together with inhibitory rate of the blood platelet aggregation of test compound when orally administered.

TABLE 5

| Test compound | Dose (mg/Kg) | No. of rats | Aggregation rate with ADP when carotid artery ring added (%) | Inhibitory rate of blood platelet aggregation (%) |
|---|---|---|---|---|
| Compound 1 of this invention | 3 | 3 | 2.7 | 48.1 |
| | 10 | 3 | 17.7 | 100 |
| | 30 | 3 | 10.0 | 100 |
| 2 | 3 | 3 | 0.0 | 39.0 |
| | 10 | 3 | 7.7 | 70.1 |
| | 30 | 3 | 1.3 | 85.5 |
| | 100 | 3 | 23.3 | 100 |
| Aspirin | 30 | 3 | 45.7 | 67.5 |
| | 100 | 3 | 58.3 | 100 |
| Non-medicated groups | | 27 | 2.8 | — |
| Comparative aggregation values | | 6 | 45.3 | — |

As shown in Table 5, blood platelet aggregation by ADP was inhibited with PGI$_2$-like substances existing in carotid artery ring in the case of the groups to which the compounds of this invention were given, whereas said phenomena could not be observed in the groups to which aspirin was given. Accordingly, the compounds of this invention is seen to hardly inhibit biosynthesis of PGI$_2$ at the dose to exert an inhibitory activity of blood platelet aggregation, unlike aspirin and thus possess superior properties as a circulatory dysfunction improving agent.

(5) Calcium antagonistic activity

Thoracic aorta was removed from male Wistar strain rats with a body weight of 350 g to 450 g and then spiral-shaped pieces of aorta were prepared therefrom. Samples were stabilized by aerating with 95% $O_2$—5% $CO_2$ and immersing in Krebs-Henseleit solution kept at 37° C. over 1 hour. Thereafter, samples were further stabilized in Krebs-Henseleit solution containing no CaCl$_2$ over 1 hour and then in a 80 mM KCl nutritive liquid wherein NaCl was exchanged with an equimolar KCl (depolarized liquid) over a further one hour. Then, samples were washed with the depolarized liquid and loaded with a static tension of 1.0 g. When CaCl$_2$ was added to the nutritive liquid so as to reach a final concentration of 10 mM, tension was produced in samples and, after 15-20 minutes from the addition of CaCl$_2$, the maximum tension was obtained. At this point, test compounds were applied and relaxing activity of test compounds was evaluated. Tension was determined in equal dimension.

Relaxation rate was calculated according to the following equation:

$$\text{Relaxation rate} = \frac{A - B}{A} \times 100 \, (\%)$$

A: Maximum tension generated
B: Generated tension retained after administration of test compound All test compounds were given in the form of a solution in dimethyl sulfoxide at a dose of 0.1 ml, whereupon a final concentration of dimethyl sulfoxide itself was adjusted to 0.5 V/V %.

The results are shown in Table 6.

TABLE 6

| Test compound | Final concentration (μM) | Relaxation (%) |
|---|---|---|
| Compound 1 of this | 3 | 8.5 |
| | 10 | 30 |

TABLE 6-continued

| Test compound | Final concentration (μM) | Relaxation (%) |
|---|---|---|
| invention | | |
| Papaverine hydrochloride | 10 | 0 |

From Table 6, it can be seen that the compounds of this invention exert a calcium antagonistic activity with concentration dependence.

(6) Action on blood flow volume and femoral artery blood pressure in carotid artery and femoral artery Male New Zealand White rabbits (body weight of 2.8 Kg to 3.5 Kg) were used and anesthetized with pentobarbital sodium. Blood flow volumes in the carotid artery and femoral artery were measured and recorded via a non-blood observing type of a probe for measuring blood flow volume. Also, blood pressure in femoral artery was simultaneously measured and recorded with measurement of blood flow.

The compound of this invention was dissolved in an aqueous solution containing 1% tartaric acid and 1% dimethylacetamide, while papaverine hydrochloride dissolved in 0.9% physiological saline. These test compounds were intravenously given through a residual polyethylene tube within femoral vein.

The results are shown in Table 7.

TABLE 7

| | Test compound | Dose (mg/Kg) | Blood flow volume in carotid artery (ml/min) | | | | Blood flow volume in femoral artery (ml/min) | |
|---|---|---|---|---|---|---|---|---|
| | | | A | B | C | D | A | B |
| Compounds of this invention | 1 | 0.01 | 15.5 ± 0.03 | 21.9 ± 4.26 | 6.3 ± 4.29 | 40.8 ± 27.63 | 19.0 ± 8.00 | 22.1 ± 10.85 |
| | | 0.05 | 14.5 ± 1.02 | 22.7 ± 6.46 | 8.1 ± 5.94 | 53.7 ± 37.70 | 18.5 ± 8.35 | 24.3 ± 11.69 |
| | | 0.1 | 15.4 ± 0.43 | 26.9 ± 5.34 | 11.5 ± 5.68 | 74.2 ± 36.40 | 18.5 ± 8.35 | 27.8 ± 9.90 |
| | | 0.5 | 17.3 ± 1.46 | 35.1 ± 8.55 | 17.8 ± 9.20 | 109.7 ± 63.77 | 19.5 ± 9.17 | 28.2 ± 11.19 |
| | 2 | 0.01 | 15.6 ± 0.05 | 19.4 ± 3.10 | 3.9 ± 3.05 | 24.9 ± 20.4 | 20.9 ± 12.9 | 26.5 ± 16.0 |
| | | 0.05 | 13.9 ± 0.87 | 17.7 ± 3.76 | 3.8 ± 2.91 | 24.8 ± 18.65 | 18.8 ± 8.12 | 20.3 ± 9.75 |
| | | 0.1 | 14.5 ± 0.65 | 22.4 ± 5.21 | 7.9 ± 5.06 | 54.3 ± 33.40 | 15.9 ± 6.46 | 12.5 ± 5.83 |
| | | 0.5 | 16.7 ± 1.67 | 32.1 ± 8.60 | 15.4 ± 8.77 | 96.0 ± 60.1 | 19.5 ± 9.12 | 13.8 ± 8.12 |
| Papaverine hydrochloride | | 0.5 | 18.6 ± 1.75 | 38.7 ± 5.31 | 20.1 ± 4.48 | 108.3 ± 25.73 | 16.8 ± 4.04 | 23.0 ± 4.91 |
| | | 1.0 | 19.3 ± 3.62 | 26.3 ± 6.31 | 7.0 ± 2.77 | 33.2 ± 7.60 | 30.1 ± 7.45 | 40.0 ± 9.82 |

| | Test compound | Dose (mg/kg) | Blood flow volume in femoral artery (ml/min) | | Blood pressure in femoral artery (mmHg) | | | |
|---|---|---|---|---|---|---|---|---|
| | | | C | D | A | B | E | F |
| Compounds of this invention | 1 | 0.01 | 3.1 ± 2.85 | 9.9 ± 7.73 | 96.0 ± 1.00 | 92.3 ± 1.45 | 3.7 ± 1.86 | 3.8 ± 1.91 |
| | | 0.05 | 5.8 ± 3.35 | 28.2 ± 3.74 | 91.7 ± 3.33 | 81.7 ± 3.28 | 10.0 ± 2.52 | 10.9 ± 2.53 |
| | | 0.1 | 9.3 ± 1.59 | 65.2 ± 18.75 | 90.0 ± 5.00 | 81.7 ± 1.67 | 8.3 ± 4.41 | 8.8 ± 4.64 |
| | | 0.5 | 8.7 ± 2.05 | 55.3 ± 11.72 | 86.7 ± 4.41 | 63.2 ± 6.65 | 23.5 ± 2.36 | 30.1 ± 2.53 |
| | 2 | 0.01 | 5.6 ± 3.10 | 28.5 ± 2.80 | 93.8 ± 1.25 | 91.3 ± 3.75 | 2.5 ± 2.5 | 2.7 ± 2.7 |
| | | 0.05 | 3.3 ± 1.75 | 13.4 ± 0.90 | 90.8 ± 3.00 | 83.7 ± 5.24 | 7.1 ± 2.32 | 8.07 ± 2.80 |
| | | 0.1 | 3.4 ± 1.25 | 23.4 ± 8.31 | 88.8 ± 3.75 | 78.1 ± 1.88 | 10.6 ± 3.59 | 11.6 ± 3.87 |
| | | 0.5 | 5.7 ± 1.17 | 36.7 ± 8.36 | 87.5 ± 4.33 | 69.2 ± 5.83 | 18.3 ± 1.67 | 21.2 ± 2.78 |
| Papaverine hydrochloride | | 0.5 | 6.1 ± 1.00 | 40.3 ± 3.80 | 94.8 ± 1.72 | 82.4 ± 2.22 | 12.4 ± 1.25 | 13.2 ± 1.39 |
| | | 1.0 | 9.8 ± 2.65 | 32.7 ± 3.73 | 91.8 ± 1.88 | 68.8 ± 4.27 | 23.1 ± 2.77 | 25.3 ± 3.34 |

A: Before administration
B: After administration
C: Increase degree
D: Increase rate (%)
E: Lowering degree
F: Lowering rate (%)

From Table 7, it can be seen that the compounds of this invention remarkably increase a blood flow volume in the common carotid artery and femoral artery and also lower a blood pressure in femoral artery.

(7) Activity to increase topical, cerebral blood flow

By using anesthatized male New Zealand White rabbits (body weight of 2.8 Kg to 3.5 Kg), effect of the compound of this invention was evaluated on topical cerebral blood flow volumes at candate nucleus and cerebral cortex according to a heat clearance method

[Acta. Physiol. Scand., 67, 1 (1966); "Kokyu to Junkan" (in Japanese), 15, 435 (1967); the Journal of the Pharmacological Society of Japan, 71, 709 (1975)]. Simultaneously, blood pressure in femoral artery was also determined. Preparation and administration of test compounds were carried out in the same manner as in the above item (6).

The results are shown in Table 8.

TABLE 8

| Test compound | Dose (mg/Kg) | Increase in topical blood flow volume (Δ μV*) | | Lowering of blood pressure in femoral artery (%) |
|---|---|---|---|---|
| | | Candate nucleus | Cerebral cortex | |
| Compound 1 of this invention | 0.3 | 0.63 ± 0.08 | 1.03 ± 0.12 | 18.2 ± 0.98 |
| | 1 | 0.85 ± 0.25 | 2.05 ± 0.29 | 30.8 ± 3.2 |
| Papaverine hydrochloride | 0.3 | 0.19 ± 0.04 | 0.57 ± 0.11 | 15.0 ± 1.2 |
| | 1 | 0.35 ± 0.07 | 1.05 ± 0.21 | 20.8 ± 3.4 |

*change in blood flow expressed in terms of voltage

From Table 8, it can be seen that the compounds of this invention remarkably increase a topical, cerebral blood flow volume and also lower a blood pressure in femoral artery.

(8) Activity to increase blood flow volume in coronary artery

A mongrel adult dog was anesthetized with pentobarbital sodium and then underwent thoracotomy under artificial respiration. After cardiac membrane was removed, the origin of branches in left coronary artery was removed from its peripheral tissues and blood flow volume of coronary artery was measured via the probe for determining blood flow which was attached to said origin. Simultaneously, blood pressure in femoral artery was measured. Preparation and administration of test compounds were carried out in the same manner as in the above item (6).

The results are shown in Table 9.

TABLE 9

| Test compound | Dose (mg/Kg) | Blood flow volume in coronery artery (ml/min.) | | | Lowering of blood pressure in femoral artery (%) |
|---|---|---|---|---|---|
| | | Before administration | After administration | Increase rate (%) | |
| Compound 1 of this invention: | 0.1 | 18.8 | 28.8 | 53.2 | 17.6 |
| | 0.3 | 18.8 | 37.5 | 99.5 | 29.4 |

From Table 9, it can be seen that the compounds of this invention remarkably increase a blood flow volume in coronary artery and also lower a blood pressure in femoral artery.

EXAMPLE 4

Formulations of the present circulatary disorder improving agent.

(1) Tablets

Components as recited below were uniformly blended in a conventional manner and then made into tablets by means of an ordinary tablet machine.

| The compound 1 of this invention | 50 mg |
|---|---|
| Crystalline cellulose | 21 mg |
| Corn starch | 33 mg |
| Lactose | 65 mg |

-continued

| Magnesium stearate | 1.3 mg |
|---|---|

(2) Tablets

Components as recited below were made into tablets in the same manner as in the above (1).

| The compound 2 of this invention | 70 mg |
|---|---|
| Crystalline cellulose | 29 mg |
| Corn starch | 46 mg |
| Lactose | 91 mg |
| Magnesium stearate | 1.8 mg |

(3) Soft Capsules

Components as recited below were uniformly blended in a conventional manner and packed into soft capsules.

| The compound 1 of this invention | 50 mg |
|---|---|
| Olive oil | 105 mg |
| Lecithin | 6.5 mg |

(4) Injectable Solution

Components as recited below were admixed and packed into a 1 ml ampoule.

| The compound 1 of this invention | 0.7 mg |
|---|---|
| Methanesulfonic acid | 2.1 mg |
| Sodium chloride | 3.5 mg |
| Injectable distilled water | 1.0 mg |

What is claimed is:

1. A 1-alkylamino-4-phenylphthalazine compound of the formula

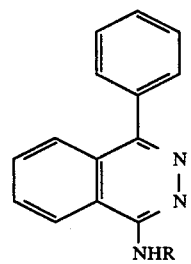

(I)

wherein R is a neopentyl group or a 1-ethylpropyl group, and pharmaceutically acceptable salts thereof.

2. 1-Neopentylamino-4-phenylphthalazine of the formula of claim 1.

3. 1-(1-Ethylpropylamino)-4-phenylphthalazine of the formula of claim 1.

4. A pharmaceutical composition comprising an effective amount of active ingredient with activity to treat ischemic cardiac diseases, cerebrovasculatory diseases and peripheral circulatory disturbance in combination with a pharmaceutical carrier, wherein said active ingredient is a compound as claimed in claim 1.

5. The pharmaceutical composition as claimed in claim 4, wherein said active ingredient is 1-neopentylamino-4-phenylphthalazine.

6. The pharmaceutical composition as claimed in claim 4, wherein said active ingredient is 1-(1-ethylpropylamino)-4-phenylphthalazine.

7. A method for the treatment of ischemic cardiac diseases, cerebrovasculatory diseases and peripheral circulatory disturbance in humans which comprises administering to humans suffering from these dysfunctions an effective amount of a compound as claimed in claim 1 for said treatment.

* * * * *